United States Patent [19]

Wallenfels

[11] 4,376,197
[45] Mar. 8, 1983

[54] INDOXYLMALTODEXTRINS, A PROCESS FOR THEIR PREPARATION AND THEIR USE

[75] Inventor: Kurt Wallenfels, Freiburg, Fed. Rep. of Germany

[73] Assignee: Behringwerke Aktiengesellschaft, Marburg an der Lahn, Fed. Rep. of Germany

[21] Appl. No.: 222,046

[22] Filed: Jan. 2, 1981

[30] Foreign Application Priority Data

Jan. 5, 1980 [DE] Fed. Rep. of Germany ....... 3000292

[51] Int. Cl.$^3$ .............................................. C08B 37/16
[52] U.S. Cl. .................................... 536/17.4; 435/22; 435/97; 435/99; 536/46
[58] Field of Search ....................................... 536/4, 46

[56] References Cited

U.S. PATENT DOCUMENTS 4,233,403  11/1980  Menson et al. ....................... 435/22

FOREIGN PATENT DOCUMENTS 2752501  5/1979  Fed. Rep. of Germany .

OTHER PUBLICATIONS

J. P. Horwitz et al., J. Medicinal Chem., 1964, vol. 7, 574–575.

*Primary Examiner*—A. Lionel Clingman
*Attorney, Agent, or Firm*—Curtis, Morris & Safford

[57] ABSTRACT

New indoxylmaltodextrins, an enzymatic process for their preparation and their use as a substrate for the analytical detection and the determination of amylases, and rapid diagnostic agents which contain such indoxylmaltodextrins are described.

2 Claims, No Drawings

INDOXYLMALTODEXTRINS, A PROCESS FOR THEIR PREPARATION AND THEIR USE

The invention relates to new indoxylmaltodextrins, the enzymatic synthesis thereof and their use as a substrate for the analytic detection and the determination of amylases, as well as to rapid diagnostic agents which contain indoxylmaltodextrins.

In clinical-chemical diagnostics, the determination of amylase both in blood serum and in urine is of great importance for the recognition of pancreatic diseases.

A number of various methods permitting quantitative determination have been described in the literature. An example is provided by German Offenlegungsschrift No. 2,731,421, according to which nitro-aromatic glycosides are used as the substrate for the determination of amylase. Reaction products of these substrates are water-soluble. The determination processes, which proceed in an aqueous system, are of significance in clinical laboratories. However, they are all labor-intensive, necessitate expensive measuring instruments for quantitative determination of the results and require technically qualified personnel. In practice, however, it is frequently necessary for the existence of pancreatic disease in a particular case to be clarified rapidly and at the patient's bedside. Numerous parts of the body which are of diagnostic interest can at present be analyzed rapidly and simply with the aid of rapid diagnostic agents, such as, for example, test strips. These analysis methods, which are frequently used for screening purposes, are thus widely used. There is likewise a need for a rapid diagnostic agent for the determination of amylase. However, the above-mentioned substrates are not suitable for this purpose.

Since the detection methods in almost all cases proceed in an aqueous medium and the reaction products are water-soluble, particular measures must be taken in producing test strips in order to prevent the reactants from being washed out or from bleeding out.

Chromogenic compounds which are reacted to give water-insoluble dyestuffs, that is to say indigo derivatives, have already been described in the literature (J. Med. Chem., Volume 7, page 574, 1964). Thus, for example, 5-bromo-4-chloroindoxyl $\beta$-D-glucoside has been described for the histochemical detection of $\beta$-glucosidase. However, these known compounds are unsuitable for the determination of amylase.

It was thus the aim and the object of the invention to develop a test which can be carried out rapidly and simply, that is to say a rapid diagnostic agent for alphaa-mylase, in which the reaction product of the substrate for the amylase has a low solubility in water and thus does not bleed. The invention is firstly based on the object of providing such a substrate for the determination of amylase.

It has now been found, surprisingly, that indoxylmaltodextrins have the desired properties.

The invention relates to indoxylmaltodextrins of the general formula:

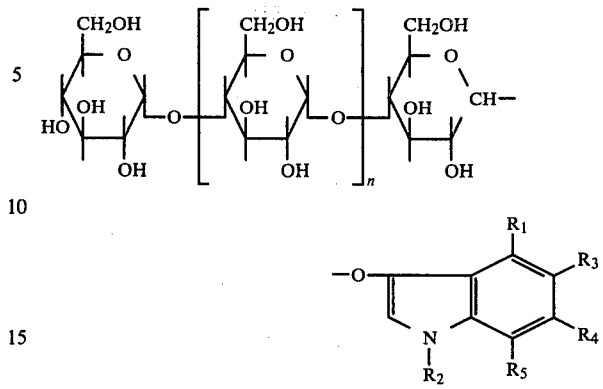

in which n is an integer from 1 to 9, $R_1$, $R_3$, $R_4$ and $R_5$ are halogen, alkyl or alkoxy with 1-5 carbon atoms, phenyl, substituted phenyl, phenoxy, substituted phenoxy, nitro or hydrogen, $R_2$ is H, lower alkyl or lower alkoxy with 1-3 C atoms in the alkyl chain and the heterosidic glucoside bond has the $\alpha$- or $\beta$-configuration.

The compounds are suitable substrates for amylases. Using these compounds, amylase activity can be determined colorimetrically in a simple manner and with a high sensitivity, and can also be used for rapid diagnostic agents.

Indoxylmaltodextrins in which n=2-4, that is to say with 4-6 glucose units, have proved particularly advantageous because of their rapid rate of conversion.

The degradation by certain amylases proceeds only down to the indoxyl glucoside or maltoside. In the case of these amylase enzymes, it has thus proved appropriate to use an $\alpha$- or $\beta$-glucosidase as an auxiliary enzyme in the determination, according to the invention, of amylase activity; these glucosidases can then rapidly further split the indoxyl glucosides or indoxyl maltosides with 3-12 glucose units which are split off from the indoxylmaltodextrin according to the invention by the amylase, to give the aglucon. If a sufficient amount of this $\alpha$- or $\beta$-glucosidase auxiliary enzyme is present in the batch, these products from the splitting reaction are then immediately split further, in the nascent state, by the auxiliary enzyme.

The indoxyl liberated is oxidized, in the presence of oxygen or other oxidizing agents, to indigo, the concentration or color intensity of which represents a measure of the amylase activity. Suitable oxidizing agents are iron-III compounds or other metal salts which have a high valency and are capable of effecting oxidation to give the indigo dyestuff. Oxidation in the presence of oxygen is best carried out with an electron-transferring compound, such as, for example, tetramethyl-p-phenylenediamine, or an enzyme. A further possibility for oxidizing the indoxyl is to use hydrogen peroxide in the presence of a catalyst, such as peroxidase, catalase or metal salts.

The reaction equations for an amylase determination according to the invention can be shown, for example, as follows:

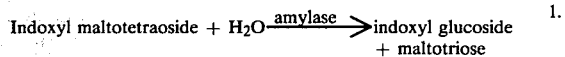

-continued

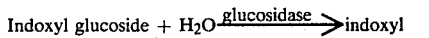  2.

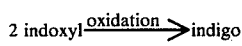  3.

The indoxyl α-D-maltodextrins, which have the indoxyl group on the reducing glucose radical of the maltodextrin and 3-12 glucose units in the chain and which are used for carrying out the determination, according to the invention, of amylase are new substances. They can be prepared, according to the invention, by enzymatic transglucanosylation, starting from indoxyl glucoside. The starting material is α-cyclodextrin and indoxyl α- or β-D-glucoside with one glucose radical. Conversion into indoxylmaltodextrins, which essentially have chain lengths of up to 12 glucose units, is effected by mixing the reactants in aqueous solution in the presence of a transglucanosylase, preferably the transglucanosylase which has been obtained from Klebsiella pneumoniae and has been described by BENDER, Arch. Mikrobiol., Volume 111 (1977), 271–282. However, the synthesis reaction can also be carried out using another transglucanosylase, for example that obtained from B. macerans, or other enzymes with a comparable specificity, for example the D-transglycosidase obtained from potatoes or other plants, that is to say those which can transfer glucanosyl radicals from linear or cyclic dextrins onto acceptors, the acceptors then being indoxyl α- or β-glucoside. The invention furthermore relates to a process for the preparation of indoxyl-α- or -β-maltodextrins, which comprises allowing an aqueous solution of α-, β- or γ-cyclodextrin and an α- or β-D-glucoside containing the indoxyl group to react in the presence of a transglucanosylase, after which the indoxyl-α- or -β-maltodextrins synthesized are isolated in a manner known per se.

The synthesis starting from α-maltosyl fluoride and α-amylase, as the transferring enzyme, is based on the following facts: α-maltosyl fluoride, prepared in accordance with the method of GENGHOF et al., Carbohydr. Res. 61 (1978) 291, is split by α-amylases, in particular from B. subtilis or the pancreas of pigs, with predominant transfer of maltosyl radicals onto maltosyl fluoride itself, so that maltodextrins with 3-6 glucose units are formed (OKADA et al., Carbohydr. Res. 71 (1979), 287). If a heteroglucoside, such as, for example, indoxyl glucoside, is used as the maltose acceptor, the corresponding indoxylmaltodextrins with 3-6 glucose units in the α-1,4-linked chain are formed. They can be separated into the individual components in a manner known per se, for example by chromatography. α-Maltosyl fluoride and α-amalyse are incubated, in concentrations of about 5.5 mmoles or 10-100 μg/ml in about 0.025 M acetate buffer of about pH 5.6, with indoxyl glucoside (about 10 mmoles). Working-up can be carried out after 1-2 hours.

Although it was known that substituted α-D-maltodextrins can be prepared by enzymatic transglucanosylation, starting from amylose, amylopectin or cyclodextrins, methyl or phenyl α-glucoside being used as the acceptor, compare FRENCH et al., J. Am. Chem. Soc., Volume 76, 2387–2390 (1954), it is nevertheless surprising that it is possible to use, as the acceptors, not only glucosides with a relatively simple structure, such as α-methyl or α-phenyl derivatives, but also those glucosides which have, as the aglucon, an indicator compound with analytical significance in the determination of the amylase enzyme.

In a preferred embodiment of the preparation process for the new indoxylmaltodextrins, the α-cyclodextrin and indoxyl glucoside are incubated in an aqueous buffered solution, in an amount determined by the solubility of the components, with the transglucanosylase, at a pH range from 4.0 to 9.0, preferably from 5.5 to 7.5, and at a temperature of 15° to 45° C. for 2 to 200 hours, preferably 30 to 50 hours, for example for about 48 hours at room temperature. 0.2 to 2 moles, preferably about 1 mole, of indoxyl glucoside and 50 to 500 mg of transglucanosylase with an activity of 45 units per mg of preparation should be employed per mole of α-cyclodextrin. After the incubation, the enzyme is inactivated, for example by heating the solution to a temperature sufficient to inactivate the enzyme, such as, for example, 70° to 90° C., preferably 85° C., for 15 minutes. The indoxylmaltodextrins are then isolated, during which purification of the product appropriate for its chain length, should be effected. It is expedient to employ a process which permits separation of saccharides of different molecular weight.

A particularly suitable method for this is chromatography, above all high pressure column chromatography. By clean preparative separation of the reaction product, it is possible to obtain the desired indoxylmaltodextrins as fractions, for example indoxyl maltotrioside and indoxyl maltotetraoside, and also the higher homologs of the series with up to 12 glucose radicals or more, and to separate them off from the free indoxyl, unreacted glucoside and glucose, maltose and higher maltosides formed, which are present in the batch.

Indoxylmaltodextrins with a chain length of 4-6 glucose radicals are particularly advantageous for the analytical determination of amylase since they are split particularly rapidly. In order to increase their yield in the process according to the invention, it is expedient to degrade the higher members of the homologous series to the desired lower members, which can be effected by treating the reaction batch with an α-glucan phosphorylase after the transglucanosylation.

An enzyme obtained from Klebsiella pneumoniae, as has been described by LINDER, KURZ, BENDER, WALLENFELS, Eur. J. Biochem, Volume 70, 291–303 (1976), is preferably used here. Nearly all the higher homologs of the series mentioned are then essentially degraded down to the maltotetraoside in this incubation, so that the yield of the compounds which are particularly interesting for the analysis can thus be substantially increased. The incubation with α-glucan phosphorylase is carried out at a pH value of 5.5 to 7.5. It is expedient for this purpose to use a phosphate buffer with a molarity of M/20 to M/10. It has been found that when arsenate buffer with a molarity of M/50 to M/100 and muscle phosphorylase are used, indoxyl maltotetraoside is essentially formed. Hydrolytic enzymes can also be used for the purpose mentioned, as long as they only split the glycosidic bonds in the peripheral area of the maltodextrins.

The process described for the preparation of indoxyl α-D-maltodextrins is generally applicable. The transfer of glucanosyl radicals onto glycosidic acceptors is independent both of the nature of the aglycon and of the configuration of the glycosidic bond with which this is bonded to the glucose. Thus, for example, indoxyl α-D- glucoside can be employed for the preparation of a series comparable to the α-anomers.

Glucosides of indoxyl derivatives, such as, for example, 5-bromo-4-chloroindoxyl glucoside, 5-methylindoxyl glucoside, 4-ethoxyindoxyl glucoside, 5-phenylindoxyl glucoside and 4-nitroindoxyl glucoside, and combined derivatives, such as 2-methyl-5-bromoindoxyl glucoside and 2-methyl-5-phenylindoxyl glucoside, are equally suitable for the enzymatic synthesis of indoxylmaltodextrins.

The indoxylmaltodextrins thus obtained are outstandingly suitable as chromogenic substrates, for the preparation of rapid diagnostic agents for amylase.

For this purpose, the substrate according to the invention, in aqueous solution, is applied to an absorbent matrix by processes known per se, together with buffer salts, detergents, accelerators or inhibitors (for example for certain isoenzymes of amylase) and any necessary auxiliary enzymes, stabilizers, thickeners and agents for imparting hydrophobic properties, and is fixed on the matrix by gentle drying.

In the simplest case, paper is used as the absorbent matrix. However, it is also possible to employ non-wovens made from plastics or water-absorbing films, in the latter case the chemicals required being cast, in the form of a film or a sheet, from a solution or suspension together with the film-forming material and the film or sheet being hardened.

The finished reagent papers, non-woven materials or films are advantageously stuck onto a stable plastic film, which gives the test system improved mechanical stability and permits hygienic handling. In principle, the choice of buffer salts is not critical, as long as possible incompatibilities of the particular system are taken into consideration (for example inhibition of α-amylase by EDTA). The pH value is advantageously in a range favorable for the action of the auxiliary enzyme and amylase (for example 5–8.5 for α-amylase and glucosidase and 4–7 for β-amylase and glucosidase).

Detergents are, for example, the known non-ionic substances of the polyethylene oxide and polyethylene oxide derivative type, such as, for example, Genapol ® or ionic compounds, such as sodium dodecyl sulfate.

Albumin, for example, can be used as the stabilizer, polyvinylpyrrolidone or gelatin can be used as the thickener and ethylcellulose can be used as the agent for providing hydrophobic properties. Alkali metal halides, in particular sodium chloride, are known as accelerators, and the natural inhibitors which are obtained from cereal seeds and have a very powerful action (German Auslegeschrift 2,003,934) are known examples of inhibitors.

Examples of the preparation and use of the substances according to the invention are described, in order to illustrate the invention:

EXAMPLE 1

1.1 Preparation of the indoxylmaltodextrins 10 mg (450 U) of transglucanosylase obtained from Klebsiella pneumoniae are added to α-cyclodextrin and indoxyl glucoside dissolved, in an approximately molar ratio, that is to say 31 g of α-cyclodextrin and 10 g of indoxyl glucoside, in 1 liter of molar 2-(N-morpholino)-ethanesulfonic acid buffer of pH 6.5, containing 0.005 mole/l of calcium chloride, and the mixture is kept at room temperature for 48 hours. The solution is then heated to 80° C. in the course of 15 minutes.

A check by thin layer chromatography shows that a homologous series of indoxylated maltodextrins containing up to 12 glucose units in the chain has been formed.

This series is separated into the individual members in several batches by high pressure liquid chromatography in a column 1 m in length and 3 cm in diameter. Biogel P ® 2, a copolymer of acrylamide and methylenebisacrylamide prepared by Bio-Rad Laboratories, Richmond, Calif., is used to fill the column. The column is developed under pressure with a pressure pump relatively free from pulsation, using pure, degassed water as the eluting agent. A parallel arrangement of a diffractometer and a spectrophotometer with flow-through cells is used as the detector. The diffractometer records the concentration of all components of the mixture according to the concentrations in which they are eluted from the column, whilst the photometer cell records only the indicated glucosides, at a wavelength of, for example, 365 nm. The glucosides are collected separately in individual vessels, according to their individual absorption maxima, by means of a fraction collector.

The following proportions of individual indoxyl glucosides were obtained: 3.0 g of indoxyl maltoside, 3.0 g of indoxyl maltotrioside, 3.1 g of indoxyl maltotetraoside and 2.5 g of indoxyl maltopentaoside.

Small amounts of higher homologs are formed (about 6 g, up to indoxyl maltododecaoside).

There are no substantial shifts in the percentage proportions of the individual indoxylmaltodextrins at other ratios.

1.2 Preparation of a test strip for the detection of α-amylase 0.1 m² of indicator base paper (150 g/m²) is impregnated with the following solution, and then dried: 1 l of triethanolamine buffer, pH 7, 50 mmoles/l, 10 g of indoxyl α-maltotetraoside and 20,000 units of α-glucosidase.

The dry reagent paper is stored under protection from moisture and light.

EXAMPLE 2

Analogously to Example 1.2, 13 g of 5-bromo-4-chloroindoxyl α-maltopentaoside are employed instead of 10 g of indoxyl α-maltotetraoside.

EXAMPLE 3

0.1 m² of indicator base paper (150 g/m²) is impregnated successively with the following solutions, and then dried.

Solution A: 1 l of citrate buffer, pH 6, 30 mmoles/l, containing 10 g of indoxyl β-maltotetraoside and 250,000 units of β-glucosidase;

Solution B: 1 l of citrate buffer, pH 6, 30 mmoles/l, containing 20,000 units of α-glucosidase.

Using test papers of this type, pathological amylase concentrations can be detected in urine after 5–8 minutes by a clearly visible green-blue coloration. A test paper modified in respect of its detection sensitivity, absorption of liquid (rate) and life is obtained by adding the abovementioned accompanying substances (accelerators, inhibitors, detergents, thickeners, agents for providing hydrophobic properties and stabilizers).

I claim:

1. Indoxylmaltodextrins which have the general formula:

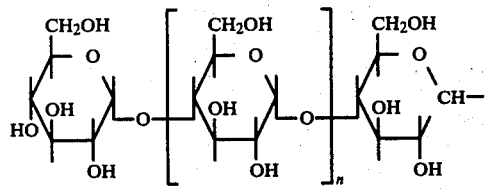

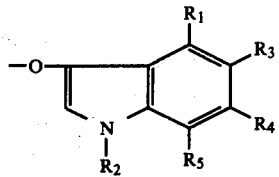

in which n is an integer from 1 to 9, $R_1$, $R_3$, $R_4$ and $R_5$ are halogen, alkyl or alkoxy with 1-5 carbon atoms, phenyl, substituted phenyl, phenoxy, substituted phenoxy, nitro or hydrogen, $R_2$ is H, lower alkyl or lower alkoxy with 1-3 C atoms in the alkyl chain and the heterosidic glucoside bond has the α- or β-configuration.

2. Indoxylmaltodextrins as claimed in claim 1, in which n is an integer from 2 to 4 and R is hydrogen.

* * * * *